United States Patent [19]

Aratani et al.

[11] Patent Number: 4,603,218
[45] Date of Patent: Jul. 29, 1986

[54] ASYMMETRIC SYNTHESIS OF CYCLOPROPANECARBOXYLATE DERIVATIVES USING CHIRAL COPPER COMPLEX AS CATALYST

[75] Inventors: Tadatoshi Aratani, Nishinomiya; Hiroshi Yoshihara, Takatsuki; Gohfu Susukamo, Ibaraki, all of Japan

[73] Assignee: Sumitomo Chemical Co., Ltd., Osaka, Japan

[21] Appl. No.: 760,507

[22] Filed: Jul. 30, 1985

Related U.S. Application Data

[62] Division of Ser. No. 614,224, May 24, 1984, Pat. No. 4,552,972.

[30] Foreign Application Priority Data

Jun. 3, 1983 [JP] Japan ................................. 58-99955

[51] Int. Cl.$^4$ .............................................. C07C 67/30
[52] U.S. Cl. ..................................... 560/102; 560/124; 560/1; 560/101
[58] Field of Search ................... 560/124, 102, 101, 1

[56] References Cited

U.S. PATENT DOCUMENTS

| | | | |
|---|---|---|---|
| 3,868,401 | 2/1975 | Aratani | 560/124 |
| 4,029,690 | 6/1977 | Aratani | 560/124 |
| 4,069,385 | 1/1978 | Araki | 560/124 |
| 4,197,408 | 4/1980 | Aratani | 560/124 |
| 4,288,387 | 9/1981 | Crosby | 560/124 |
| 4,344,894 | 8/1982 | Laidler | 560/124 |

*Primary Examiner*—Michael L. Shippen
*Attorney, Agent, or Firm*—Wenderoth, Lind & Ponack

[57] ABSTRACT

A chiral copper complex which is produced by the reaction of a chiral copper complex of the formula:

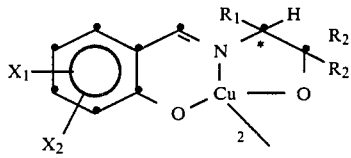

wherein $R_1$ is (a) alkyl group, or (b) aralkyl group; $R_2$ is (a) 2-alkoxyphenyl group, or (b) 2-alkoxy-5-alkylphenyl group; either one of $X_1$ and $X_2$ is (a) hydrogen atom, (b) halogen atom, (c) alkyl group, (d) alkoxy group, or (e) nitro group, or adjacent $X_1$ and $X_2$ together form a benzo group, with a mono-substituted hydrazine of the formula:

$R_3NHNH_2$ wherein $R_3$ is (a) aryl group, (b) aralkyl group, or (c) alkyl group.

The copper complex is used as a catalyst in the production of an optically active alkyl cyclopropanecarboxylate.

3 Claims, No Drawings

ASYMMETRIC SYNTHESIS OF CYCLOPROPANECARBOXYLATE DERIVATIVES USING CHIRAL COPPER COMPLEX AS CATALYST

This application is a division of application Ser. No. 614,224, filed May 24, 1984, now U.S. Pat. No. 4,552,972.

This invention relates to a novel chiral copper complex and to a process for the production of an optically active alkyl cyclopropanecarboxylate using the novel chiral copper complex as a catalyst.

More particularly, this invention relates to a novel chiral copper complex which is produced by the reaction of a chiral copper complex of the formula (1):

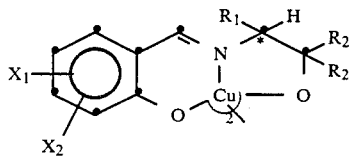

wherein $R_1$ is (a) alkyl group, or (b) aralkyl group; $R_2$ is (a) 2-alkoxyphenyl group, or (b) 2-alkoxy-5-alkylphenyl group; either one of $X_1$ and $X_2$ is (a) hydrogen atom, (b) halogen atom, (c) alkyl group, (d) alkoxy group, or (e) nitro group, or adjacent $X_1$ and $X_2$ together form a benzo group,
with a mono-substituted hydrazine of the formula (2):

wherein $R_3$ is (a) aryl group, (b) aralkyl group, of (c) alkyl group.

This invention further relates to a process for the production of an optically active alkyl cyclopropanecarboxylate which comprises the reaction of an alkyl diazoacetate of the formula (3):

wherein R is an alkyl group,
with a prochiral olefin of the formula (4):

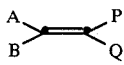

wherein each one of A, B, P and Q is selected from the group consisting of (a) hydrogen atom, (b) alkyl groups, (c) aralkyl groups, (d) aryl groups, (e) alkenyl groups, (f) alkyl groups containing halogen atom(s), and (g) alkenyl groups containing halogen atom(s),
in the presence of a catalytic amount of the novel chiral copper complex as is produced as above.

Certain kinds of optically active cyclopropanecarboxylic acids are important intermediates in the production of pharmaceuticals and agrochemicals. For example (+)-2,2-dimethyl-3-(2-methyl-1-propenyl)cyclopropanecarboxylic acid (i.e. chrysanthemic acid) is an acid component of naturally occurring insecticide, chrysanthemum flower extract, and is industrially produced as an intermediate of synthetic pyrethroid; (+)-2,2-dimethyl-3-(2,2-dichlorovinyl) or 2,2-dibromovinyl)-cyclopropanecarboxylic acid is known to be more effective than (+)-chrysanthemic acid as an acid component of the said insecticides; (+)-2,2-dimethyl-3-(2,2,2-trichloroethyl or 2,2,2-tribromoethyl)-cyclopropanecarboxylic acid can be a precursor for the above-mentioned compound; and (+)-2,2-dimethylcyclopropanecarboxylic acid has been discovered as an effective constituent of a dehydropeptitase inhibitor for a new type of antibiotics such as Thienamycin derivatives (Japanese Patent Kokai Nos. 40669/80 and 51023/80).

The methods are available for the production of an optically active cyclopropanecarboxylic acids. One is an optical resolution of racemic mixture and the other is a direct asymmetric synthesis. The latter can be more efficient than the former. From industrial point of view, asymmetric synthesis using chiral metal complexes is as important as asymmetric reaction utilizing enzymes.

We have been working on the asymmetric synthesis of chrysanthemic acid or its ester, and have already disclosed a method of producing optically active alkyl chrysanthemate, characterized by reacting 2,5-dimethyl-2,4-hexadiene with an alkyl diazoacetate in the presence of a copper complex having a chiral ligand [Cu(L*)n] (U.S. Pat. No. 3,868,401).

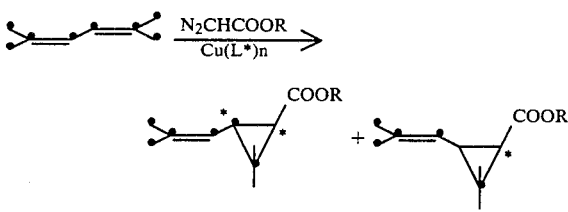

We have further found that the chiral copper complex of the formula (1) is especially effective as a catalyst for the above asymmetric synthesis (U.S. Pat. No. 4,029,690).

We have also found that the chiral copper complex of the formula (1) is effective for the asymmetric synthesis of general cyclopropanecarboxylic acid (Japanese Patent Kokai No. 160241/75).

The prochiral olefins of the general formula (4) give optically active alkyl cyclopropanecarboxylates of the general formulas (5) and (6).

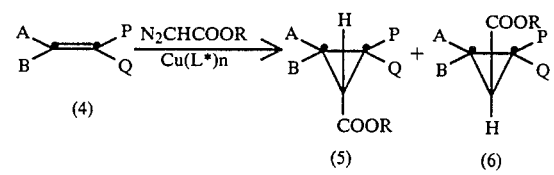

wherein A, B, P and Q are as defined as before.

As for the term "prochiral," reference may be made, for example, to "Bunshi No Katachi To Taisho" by Masao Nakazaki, Nankodo, Tokyo, 1969.

In carrying out this asymmetric reaction in industrial scale, there has been the following problem: As is well known, alkyl diazoacetates are explosive compounds. It is necessary, therefore, to keep the concentration of this compound in the reaction system as low as possible. In fact, alkyl diazoacetate is usually added dropwise to a mixture of olefin and catalyst. The decomposition of the diazoacetate can be monitored by the nitrogen gas evolved. Further, it is necessary that the copper complex used as a catalyst should be activated beforehand so that it reacts smoothly with alkyl diazoacetate.

For the activation of the copper complex of the general formula (1), the following method has been employed: A mixture of the copper complex, olefin and a small amount of alkyl diazoacetate is gradually heated to 70°-80° C. until the evolution of nitrogen gas is observed. The copper complex once activated is sensitive enough to decompose alkyl diazoacetate instantly even at a lower temperature.

However, this activation method is too troublesome as a practical operation, and moreover the instantaneous decomposition of the accumulated alkyl diazoacetate, even though it may be a low concentration, is dangerous.

Especially, when an olefin of low boiling point or a solvent of low boiling point is used, the heating operation itself can not be applicable. This is the reason why a more secure and a more safe method than the heat-activation is required.

We made much effort to solve this practical problem, and as a result, we have found that a new chiral copper complex, which is produced by reacting a chiral copper complex of the general formula (1) with a monosubstituted hydrazine of the general formula (2), is far more active than chiral copper complex of the formula (1) as a catalyst for the decomposition of alkyl diazoacetate.

The structure of the new chiral copper complex produced is not yet elucidated confirmly, but the following formula (7) is proposed as a possible structure:

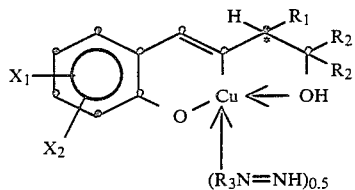

wherein $R_1$, $R_2$, $X_1$, $X_2$ and $R_3$ are as defined before.

The new complex of the general formula (7) is supposed to be a copper (I) complex. The four coordination sites of the copper (I) is occupied by a Schiff base as a tridentate ligand and by a half of diazene $R_3NH=NH$ as a bidentate ligand. In this connection it should be noted that the reaction of hydrazine with a divalent inorganic copper salt produces a diazene-copper (I) complex [J. Am. Chem. Soc., 92, 428 (1970) and Accounts Chem. Res. 4, 193 (1971)].

That is to say, the main feature of this invention is the discovery of a novel chiral copper complex produced by reacting a chiral copper complex of the general formula (1) with a monosubstituted hydrazine of the general formula (2), and its application, as a catalyst, to the asymmetric synthesis of an alkyl cyclopropanecarboxylate.

In this invention, the alkyl groups mean those containing 1 to 8 carbon atoms, for example, methyl, ethyl, propyl, isopropyl, butyl, isobutyl, 2-butyl, t-butyl, hexyl, octyl, etc., however, lower alkyl groups containing 1 to 4 carbon atoms are suitable.

The aralkyl groups are phenylalkyl groups, in other words, alkyl groups of 1 to 3 carbon atoms substituted by a phenyl group, for example, benzyl group.

The aryl groups are phenyl, tolyl, xylyl and so on.

The alkoxy groups are those containing 1 to 8 carbon atoms such as methoxy, ethoxy, propoxy, isopropoxy, butoxy, t-butoxy, hexyloxy, octyloxy, etc.

The halogen atoms are chlorine atom and bromine atom.

Specific examples of preferable 2-alkoxyphenyl groups are 2-methoxyphenyl; 2-ethoxyphenyl; 2-propoxyphenyl; 2-isopropoxyphenyl; 2-butoxyphenyl; 2-t-butoxyphenyl and 2-octyloxyphenyl; and preferable examples of 2-alkoxy-5-alkyl-phenyl groups include 2-methoxy-5-methylphenyl; 2-butoxy-5-methylphenyl; 5-methyl-2-octyloxyphenyl; 2-butoxy-5-t-butylphenyl; and 5-t-butyl-2-octyloxyphenyl.

The chiral copper complex of the general formula (1) can be produced by the reaction of a chiral Schiff base of the general formula (8):

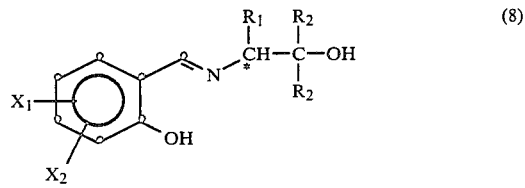

wherein $R_1$, $R_2$, $X_1$ and $X_2$ are as defined before, with a suitable cupric salt (U.S. Pat. No. 4,029,683).

Examples of the chiral Schiff base of the general formula (8) including the following compounds. Either (R) form or (S) form may be used: N-salicylidene-2-amino-1,1-di(2-methoxyphenyl)-3-phenyl-1-propanol; N-salicylidene-2-amino-1,1-di(2-isopropoxyphenyl)-3-phenyl-1-propanol; N-salicylidene-2-amino-1,1-di(2-butoxy-5-t-butylphenyl)-3-phenyl-1-propanol; N-salicylidene-2-amino-1,1-di(2-butoxy-butoxy-5-t-butylphenyl)-1-propanol; N-salicylidene-2-amino-1,1-di(5-t-butyl-2-octyloxyphenyl)-3-phenyl-1-propanol; N-salicylidene-2-amino-1,1-di(5-t-butyl-2-octyloxyphenyl)-1-propanol; N-(3-methoxy-salicylidene)-2-amino-1,1-di(2-butoxy-5-t-butylphenyl)-3-phenyl-1-propanol; N-(3-ethoxysalicylidene)-2-amino-1,1-di(2-isopropoxyphenyl)-3-phenyl-1-propanol; N-(3,5-dibromosalicylidene)-2-amino-1,1-di(2-isopropoxyphenyl)-3-phenyl-1-propanol; N-(2-hydroxy-1-naphthylmethylene)-2-amino-1,1-di(2-isopropoxyphenyl)-3-phenyl-1-propanol; etc.

The chiral Schiff base (8) is produced by the reaction of a chiral amino alcohol of the general formula (9) with a salicylaldehyde derivative of the general formula (10).

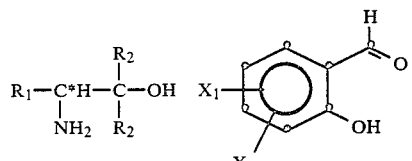

wherein $R_1$, $R_2$, $X_1$ and $X_2$ are as defined before.

As the salicylaldehyde derivatives (10), the following compounds can be cited as examples: salicylaldehyde; o-vanillin; 3-ethoxy-salicylaldehyde; 3,5-dibromosalicylaldehyde; 5-chlorosalicylaldehyde; 3-nitrosalicylaldehyde; 3-isopropyl-6-methylsalicylaldehyde; 2-hydroxy-1-naphthaldehyde; 1-hydroxy-2-naphthaldehyde; etc.

The novel chiral copper complex of this invention is produced by the reaction of a chiral copper complex of the general formula (1) with a monosubstituted hydrazine of the general formula (2).

This reaction is usually carried out in a solvent and is completed within 30 minutes. The required amount of the monosubstituted hydrazine (2) is 0.5 mol per one gram atom of the copper.

It is recommended to use the solvents that can dissolve both of the copper complex (1) and the monosubstituted hydrazine (2). Suitable solvents include aromatic hydrocarbons such as benzene, toluene, xylene, etc.; aliphatic hydrocarbons such as pentane, hexane, heptane, etc.; halogenated hydrocarbons such as methylene chloride, ethylene chloride, chlorobenzene, etc. or a mixture of the above solvents. Prochiral olefins (4) may be used also as solvents.

Since the novel chiral complex supposed to contain copper (I) ion is easily oxidized by oxygen, the reaction system should be free from any kind of oxidant such as oxygen.

Next, an explanation is made on the asymmetric synthesis of alkyl cyclopropanecarboxylate (the general formulas (5) and (6) by the reaction of a prochiral olefin of the general formula (4) with an alkyl diazoacetate.

The alkyl diazoacetate to be used as a starting material in this reaction is of the formula (3):

$$N_2CHCOOR \qquad (3)$$

wherein R is an alkyl group, preferably ethyl or t-butyl.

As for A, B, P or Q of the formula (4), the alkenyl groups are those containing 2 to 6 carbon atoms such as vinyl or isobutenyl group. Examples of the alkyl groups or alkenyl groups containing halogen atom(s) are chloromethyl, 2,2,2-trichloroethyl, 2,2,2-tribromoethyl, 2,2-dichlorovinyl, etc.

Examples of the prochiral olefins of the general formula (4) include 1-substituted ethylene derivatives such as 1-octene; styrene; 4-chloro-1-butene, etc.; 1,1-disubstituted ethylene derivatives such as isobutylene; 1,1-diphenylethylene; α-methylstyrene, etc.; trans-1,2-disubstituted ethylene derivatives such as t-4-octene; t-β-methylstyrene; t-stilbene, etc.; cis-1,2-disubstituted ethylene derivatives such as c-2-pentene; c-2-heptene; c-β-methylstyrene, etc.; 1,1,2-trisubstituted ethylene derivatives such as 2-methyl-2-butene; 2-methyl-1-phenyl-1-propene; 2,5-dimethyl-2,4-hexadiene; 1,1-dichloro-4-methyl-1,3-pentadiene; 1,1,1-trichloro-4-methyl-3-pentene; 1,1,1-tribromo-4-methyl-3-pentene, etc.; 1,1,2,2-tetrasubstituted ethylene derivatives such as 2,3-dimethyl-2-pentene; 2-methyl-3-phenyl-2-butene; etc.

In this reaction, the novel chiral copper complex produced by the reaction of a chiral copper complex of the general formula (1) with a monosubstituted hydrazine of the general formula (2) by the above-mentioned method, is used as the catalyst. At this time, there is no need of isolating the novel chiral copper complex prior to the reaction.

To explain in more detail, a prochiral olefin of the general formula (4) is dissolved in a catalyst solution prepared beforehand using a solvent, and then a diazoacetic acid ester is added dropwise. In another case, a diazoacetic acid ester is added dropwise to a solution obtained by reacting a chiral copper complex of the general formula (1) with a monosubstituted hydrazine of the general formula (2) in a mixture of said olefin and a solvent or in said olefin only. In every case, the suitable amount of the chiral copper complex of the general formula (1) is in the range of 0.01 to 0.0001 equivalent based on the diazoacetic acid ester.

The feasible reaction temperature is between 0° C. and the boiling point of the solvent used, and the suitable temperature is usually between 0° C. and 50° C.

The optically active cyclopropanecarboxylic acid esters of the general formulas (5) and (6) can be isolated by a usual method, for example, by distillation.

As regards the alkyl cyclopropanecarboxylate of the general formulas (5) and (6), no special explanation is needed because they are cyclo-adducts of alkoxycarbonylcarbene to the olefin of the general formula (4).

Among such esters, industrially important compounds and the corresponding olefins are listed as follows:

2,2-dimethylcyclopropanecarboxylic acid ester-(isobutylene); chrysanthemic acid ester(2,5-dimethyl-2,4-hexadiene); 2,2-dimethyl-3-(2,2-dichlorovinyl)cyclopropanecarboxylic acid ester(1,1-dichloro-4-methyl-1,3-pentadiene); and 2,2-dimethyl-3-(2,2,2-trichloroethyl)cyclopropanecarboxylic acid ester(1,1,1-trichloro-4-methyl-3-pentene).

This invention will be explained in detail by the following examples. However, it should be understood that the invention is not limited to these examples.

EXAMPLE 1

An amount of 0.14 g (0.097 mmol) of the copper complex of (R)-N-salicylidene-2-amino-1,1-di(2-butoxy-5-t-butylphenyl)-3-phenyl-1-propanol [corresponding to the general formula (1) wherein $R_1$=benzyl, $R_2$=2-butoxy-5-t-butylphenyl, $X_1=X_2$=hydrogen atom; $[\alpha]_{546}= +890°$ (c 0.10, toluene)] was dissolved in anhydrous toluene (10 ml) saturated with nitrogen gas, and then the atmosphere of the reaction vessel was replaced with nitrogen gas. The optical rotation $\alpha_{546}$ was $+1.25°$ (1 cm). To this solution, phenylhydrazine (10 mg, 0.093 mmol, 0.5 molar equivalent to one g atom of copper) was added at 20° C. under stirring. The reaction mixture turned from bluish green to pale yellow within five minutes. The optical rotation $\alpha_{546}$ of the solution was $-0.038°$ (1 cm). Some of the chemical properties of the novel chiral copper complex solution produced were as follows:

(1) When a toluene solution of ethyl diazoacetate (40%, 0.3 g, 1.1 mmol) was added to the above-mentioned solution at 20° C., nitrogen gas (24 ml) was evolved immediately.

(2) When the above-mentioned pale yellow solution was allowed to stand in an open atmosphere, it turned to green gradually. The optical rotation $\alpha_{546}$ was $+1.01°$ (1 cm) after one week.

EXAMPLE 2

Exactly the same operation as in Example 1 was conducted, using t-butylhydrazine (8 mg, 0.5 molar equivalent to one g atom of copper) in place of phenylhydrazine (10 mg). The optical rotation $\alpha_{546}$ of thus produced pale yellow solution was $-0.011°$ (1 cm). When ethyl diazoacetate (0.12 g) was added to this solution, quantitative amount of nitrogen gas (24 ml) was evolved instantaneously.

EXAMPLE 3

An amount of 0.40 g (0.28 mmol) of the copper complex of (R)-N-salicylidene-2-amino-1,1-di(2-butoxy-5-t-butylphenyl)-3-phenyl-1-propanol (the same complex as in Examples 1 and 2) was dissolved in toluene (50 ml), and the atmosphere of the reaction vessel was completely replaced with nitrogen gas. In this solution, isobutylene (14 g) was dissolved at 40° C., and a toluene solution of phenylhydrazine (10%, 0.3 ml, 0.28 mmol) was added. The color of the solution turned from green to yellow.

A toluene solution (40.0 g) of ethyl diazoacetate (16.15 g, 141.7 mmol) purified by distillation was added dropwise under stirring at 40° C., in the course of 7 hours. During these hours, isobutylene gas (33 g) was blown into the solution. The evolution of nitrogen gas started as soon as the addition was started, and at the end of addition, a quantitative amount of nitrogen gas (3.4 liters) was evolved. The reaction mixture was heated to 80° C. to evaporate an excess of isobutylene. The resulting mixture (105.2 g) was analyzed by gas chromatography to reveal that the content of ethyl 2,2-dimethylcyclopropanecarboxylate was 15.7% or 16.5 g, and the yield based on ethyl diazoacetate was calculated to be 82.0%. The ester was isolated by distillation under reduced pressure (boiling point 80° C./60 mmHg) to show a specific optical rotation $[\alpha]_D$ of +105.6° (c 2.0, chloroform). Based on the specific optical rotation $[\alpha]_D + 120°$ of the optically pure sample, the optical purity of the product was calculated to be 88.0%.

EXAMPLE 4

The reaction was carried out in exactly same way as in Example 3, except that, in place of a toluene solution of phenylhydrazine a toluene solution of t-butylhydrazine (10%, 0.24 ml, 0.28 mmol) was employed. The analysis of the resulting product (105.2 g) showed that the content of ethyl 2,2-dimethylcyclopropanecarboxylate was 15.3% (16.1 g) and the yield based on ethyl diazoacetate was calculated to be 80%.

The ester isolated by distillation under reduced pressure showed a specific rotation $[\alpha]_D$ of +104.4° (c 2.0, chloroform). The optical purity was calculated to be 87.0%.

EXAMPLE 5

An amount of 0.23 g (0.15 mmol) of the copper complex of (R)-N-salicylidene-2-amino-1,1-di(5-t-butyl-2-octyloxyphenyl)-1-propanol (corresponding to the general formula (1) wherein $R_1$=methyl, $R_2$=5-t-butyl-2-octyloxyphenyl, $X_1=X_2$=hydrogen atom) was dissolved in 2,5-dimethyl-2,4-hexadiene (16.53 g, 150.3 mmol). Nitrogen gas was blown into this solution to replace the atmosphere of the reaction vessel by nitrogen, and thereafter phenylhydrazine (24 mg, 0.22 mmol) was added. A mixture of ethyl diazoacetate (purified by distillation, bath temperature 40° C./1 mmHg; 8.55 g, 75 mmol) and 2,5-dimethyl-2,4-hexadiene (16.53 g, 150.3 mmol) was added at 40° C., in 5.5 hours. In the course of addition, the reaction mixture gradually turned from green to reddish brown. The constant evolution of nitrogen gas (1.8 liters in total) started as soon as the addition was started, and there was no need of heating.

The amount of ethyl chrysanthemate produced was 9.95 g by gas chromatography and the yield based on ethyl diazoacetate was 67.7%.

After distillation of 2,5-dimethyl-2,4-hexadiene (boiling point 51° C./30 mmHg) from the reaction mixture, ethyl chrysanthemate (boiling point 59° C./0.5 mmHg) was isolated. Cis/trans=48.7/51.3; $[\alpha]_D$=13.26° (neat, 1 dm). The ethyl chrysanthemate was hydrolyzed with alkali, and the chrysanthemic acid produced was converted into chrysanthemic acid chloride. The acid chloride was reacted with an excess of (+)-2-octanol in the presence of pyridine and the resulting diastereomeric ester was analyzed by gas chromatography (capillary column). (+)-cis isomer 40.50%; (−)-cis isomer 8.27%; (+)-trans isomer 44.27%; (−)-trans isomer 6.97%. The e.e. was calculated to be 66.1% for the cis isomer and 72.8% for the trans isomer.

EXAMPLE 6

An amount of 0.70 g (0.42 mmol) of the copper complex of (S)-N-salicylidene-2-amino-1,1-di(5-t-butyl-2-octyloxyphenyl)-3-phenyl-1-propanol (corresponding to the general formula (1) wherein $R_1$=benzyl, $R_2$=5-t-butyl-2-octyloxyphenyl, $X_1=X_2$=hydrogen atom) was dissolved in a mixture of toluene (50 ml) and 2-methyl-2-butene (34 g, 485.7 mmol). To this solution was added a toluene solution of benzylhydrazine (10%, 0.60 ml, 0.49 mmol) to change the color of solution from bluish green to orange yellow. Further, a toluene solution (59.7 g) of ethyl diazoacetate (23.88 g, 209.5 mmol) was added at 30° C. in 10 hours. The evolution of nitrogen gas started as soon as the addition was initiated and stopped at the end of the addition (the total volume was 5.0 liters).

The amount of ethyl 2,2,3-trimethylcyclopropanecarboxylate produced was estimated to be 22.9 g by gas chromatographic analysis, and the yield based on ethyl diazoacetate was calculated to be 70.0%. A sample isolated by distillation (boiling point: 105° C./100 mmHg) showed a cis/trans ratio of 79/21 and an optical rotation $[\alpha]_D$ of −44.7° (neat, 1 dm).

The ester was hydrolyzed with a 0.9 equivalent of alkali. The unreacted ester recovered (6%) was shown to be cis-isomer having an optical rotation $[\alpha]_D$ of −53.0° (neat, 1 dm). The carboxylic acid (92%) obtained from aqueous portion showed a a specific optical rotation $[\alpha]_D$ of −68.6° (c 1.8, chloroform).

Cis-2,2,3-trimethylcyclopropanecarboxylic acid obtained by alkaline hydrolysis of the above cis-ester showed a specific optical rotation $[\alpha]_D$ of −69.31° (c 2.3, chloroform). For optically active 2,2,3-trimethylcyclopropanecarboxylic acids, reference may be made to Agr. Biol. Chem., 37, 2235 (1973).

EXAMPLE 7

An amount of 0.12 g (0.08 mmol) of the copper complex of (R)-N-salicylidene-2-amino-1,1-di(2-butoxy-5-t-butylphenyl)-3-phenyl-1-propanol (corresponding to the general formula (1) wherein $R_1$=benzyl, $R_2$=2-butyoxy-5-t-butylphenyl, $X_1=X_2$=hydrogen atom) was dissolved in 2,5-dimethyl-2,4-hexadiene (17.6 g, 160 mmol). After the atmosphere of the reaction vessel was completely replaced by nitrogen, methylhydrazine (3.7 mg, 0.08 mmol) was added.

Thereafter, a mixture of t-butyl diazoacetate (5.68 g, 40 mmol) and 2,5-dimethyl-2,4-hexadiene (4.4 g, 40 mmol) was added dropwise at 50° C. in 4 hours. In the course of addition, the color of reaction mixture turned gradually from green to reddish brown. The constant evolution of nitrogen gas (0.96 liter in total) started as soon as the addition was initiated, so that there was no need of heating for the activation of the copper complex (1).

The amount of t-butyl chrysanthemate produced was estimated to be 6.45 g by gas chromatography, and the yield based on t-butyl diazoacetate was 72%.

After distillation of 2,5-dimethyl-2,4-hexadiene from the reaction mixture, t-butyl chrysanthemate (boiling point 82° C./0.5 mmHg) was isolated. Cis/trans=24/76, $[\alpha]_D$=+5.40 (neat, 1 dm).

t-Butyl chrysanthemate was hydrolyzed in the presence of p-toluenesulfonic acid, and the chrysanthemic acid produced was converted into the diastereomeric (+)-2-octyl ester, which was analyzed by gas chromatography. The results were: (+)-cis, 15.3%; (−)-cis, 5.8%; (+)-trans, 69.4%; (−)-trans, 9.5%. The e.e. was calculated to be 45% for the cis isomer and 76% for the trans isomer.

EXAMPLE 8

An amount of 0.28 g (0.20 mmol) of the copper complex of (S)-N-salicylidene-2-amino-1,1-di(2-butoxy-5-t-butylphenyl)-4-methyl-1-pentanol (corresponding to the general formula (1) wherein $R_1$=isobutyl, $R_2$=2-butoxy-5-t-butylphenyl, $X_1$=$X_2$=hydrogen atom) was dissolved in 1,1,1-trichloro-4-methyl-3-pentene (32.1 g, 171 mmol). After the atmosphere of the reaction vessel was completely replaced with nitrogen, phenylhydrazine (21.6 mg, 0.20 mmol) was added.

Then, a mixture of ethyl diazoacetate (2.28 g, 20 mmol) and the above-mentioned olefin (5.60 g, 30 mmol) was added dropwise at 30° C. in 6 hours. In the course of the addition, the reaction mixture gradually turned from yellow to reddish brown. The evolution of nitrogen gas (0.44 liter in total) started as soon as the addition was initiated so that there was no need of heating for the activation of the copper complex (1).

The amount of ethyl 2,2-dimethyl-3-(2,2,2-trichlorethyl)-cyclopropanecarboxylate produced was estimated to be 2.73 g by gas chromatography and the yield based on ethyl diazoacetate was 50%.

After an excess of the olefin was distilled from the reaction mixture, the ethyl ester was isolated by distillation (b.p. 90° C./0.5 mmHg). Cis/trans=88/12 (according to gas chromatographic analysis)

Ethyl 2,2-dimethyl-3-(2,2,2-trichloroethyl)cyclopropanecarboxylate was hydrolyzed with caustic potash to give 2,2-dimethyl-3-(2,2-dichlorovinyl)-cyclopropanecarboxylic acid, and was converted into the diastereomeric (+)-octyl ester, which was analyzed by gas chromatography. The results were: (+)-cis, 83.6%; (−)-cis, 3.9%; (+)-trans, 7.5%; (−)-trans, 5.0%. The e.e. was calculated to be 91% for the cis isomer and 20% for the trans isomer.

EXAMPLE 9

An amount of 0.31 g (0.22 mmol) of the copper complex of (R)-N-(3-ethoxysalicylidene)-2-amino-1,1-di(2-isopropoxyphenyl)-3-phenyl-1-propanol (corresponding to the general formula (1) wherein $R_1$=benzyl, $R_2$=2-isopropoxyphenyl, $X_1$=3-ethoxy, $X_2$=hydrogen atom) was dissolved in styrene (10.0 g, 96 mmol). After the atmosphere of the reaction vessel was completely replaced with nitrogen phenylhydrazine (23.8 mg, 0.22 mmol) was added.

Then a mixture of ethyl diazoacetate (5.0 g, 44 mmol) and styrene (10.0 g, 96 mmol) was added dropwise at 40° C. in 5 hours. At the beginning of the addition the reaction mixture gradually turned from green to reddish brown. The generation of nitrogen gas started as soon as the addition was initiated, so that there was no need of heating.

The amount of the ethyl 2-phenylcyclopropanecarboxylate produced was estimated to be 6.26 g by gas chromatography, and the yield based on ethyl diazoacetate was 75%.

After an excess of styrene was distilled from the reaction mixture, the ethyl ester was isolated by distillation (b.p. 85° C./0.5 mmHg), to shown Cis/trans=30/70 (according to gas chromatographic analysis) and $[\alpha]_D$=+72.8° (neat, 1 dm). The ester was hydrolyzed with caustic potash to give 2-phenylcyclopropanecarboxylic acid (b.p. 125° C./0.5 mmHg); $[\alpha]_D$=+89.2° (c 5.2, chloroform).

EXAMPLE 10

An amount of 0.62 g (0.44 mmol) of the copper complex of (R)-N-(2-hydroxy-1-naphthylmethylene)-2-amino-1,1-di(2-isopropoxyphenyl)-3-phenyl-1-propanol (corresponding to the geneal formula (1) wherein $R_1$=benzyl, $R_2$=2-isopropoxyphenyl, $X_1$,$X_2$=5,6-benzo) was dissolved in 1-octene (11.2 g, 100 mmol). After the atmosphere of the reaction vessel was thoroughly replaced with nitrogen, phenylhydrazine (47.5 mg, 0.44 mmol) was added.

Then a solution of ethyl diazoacetate (5.0 g, 44 mmol) in 1-octene (11.2 g, 100 mmol) was added dropwise at 50° C. in 5 hours. In the beginning of the addition, the color of reaction mixture turned gradually from yellow to reddish brown. The evolution of nitrogen gas started as soon as the addition was initiated so that there was no need of heating to induce the decomposition of diazoacetate.

The amount of ethyl 2-hexylcyclopropanecarboxylate produced was estimated to be 5.05 g by gas chromatography, and the yield based on ethyl diazoacetate was 58%.

After an excess of 1-octene was distilled from the reaction mixture, the ethyl ester was isolated by distillation (b.p. 88° C./0.5 mmHg). Cis/trans=34/66 (according to gas chromatographic analysis); $[\alpha]_D$=+24.4° (neat, 1 dm). The ester was hydrolyzed with caustic potash to give 2-hexylcyclopropanecarboxylic acid (b.p. 110° C./0.5 mmHg). $[\alpha]_D$=+36.2° (c 5.0, chloroform).

What we claim is:

1. A process for the production of an optically active alkyl cyclopropanecarboxylate which comprises reacting an alkyl diazoacetate of the formula:

wherein R is an alkyl group,
with a prochiral olefin of the formula:

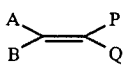

wherein each one of A, B, P and Q is selected from the group consisting of (a) a hydrogen atom, (b) alkyl groups, (c) aralkyl groups, (d) aryl groups, (e) alkenyl groups, (f) alkyl groups containing halogen atom(s), and (g) alkenyl groups containing halogen atom(s), in the presence of a catalytic amount of a chiral copper complex produced by the reaction of a chiral copper complex of the formula:

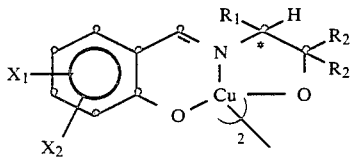

wherein $R_1$ is (a) an alkyl group, or (b) an aralkyl group; $R_2$ is (a) a 2-alkoxyphenyl group, or (b) a 2-alkoxy-5-alkylphenyl group; either one of $X_1$ and $X_2$ is (a) a hydrogen atom, (b) a halogen atom, (c) an alkyl group, (d) an alkoxy group, or (e) a nitro group, or adjacent $X_1$ and $X_2$ together form a benzo group, with a mono-substituted hydrazine of the formula:

$R_3NHNH_2$ wherein $R_3$ is (a) aryl group, (b) aralkyl group, or (c) alkyl group.

2. The process of claim 1, in which (R) is (a) ethyl, or (b) t-butyl.

3. The process of claim 1, in which said prochiral olefin is
(a) isobutylene,
(b) 2,5-dimethyl-2,4-hexadiene,
(c) 1,1,1-trichloro-4-methyl-3-pentene,
(d) 2-methyl-2-butene,
(e) 1-octene, or
(f) styrene.

* * * * *